(12) United States Patent
Kim

(10) Patent No.: US 10,479,894 B2
(45) Date of Patent: Nov. 19, 2019

(54) SOLUTION FOR FABRICATING NANO PARTICLES

(71) Applicant: SK INNOVATION CO., LTD., Seoul (KR)

(72) Inventor: Jun-Hyung Kim, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 15/666,007

(22) Filed: Aug. 1, 2017

(65) Prior Publication Data

US 2017/0335113 A1  Nov. 23, 2017

Related U.S. Application Data

(63) Continuation-in-part of application No. 14/958,366, filed on Dec. 3, 2015, now abandoned.

(30) Foreign Application Priority Data

| Dec. 3, 2014 | (KR) | 10-2014-0172290 |
| Dec. 3, 2014 | (KR) | 10-2014-0172291 |
| Dec. 24, 2014 | (KR) | 10-2014-0187801 |
| Dec. 24, 2014 | (KR) | 10-2014-0187804 |
| Jun. 12, 2015 | (KR) | 10-2015-0083451 |
| Jun. 12, 2015 | (KR) | 10-2015-0083452 |

(51) Int. Cl.

| *C09D 1/00* | (2006.01) |
| *B22F 9/24* | (2006.01) |
| *C07F 7/02* | (2006.01) |
| *C08G 77/58* | (2006.01) |
| *C23C 18/44* | (2006.01) |
| *C08K 3/10* | (2018.01) |
| *B05D 1/00* | (2006.01) |
| *B05D 1/18* | (2006.01) |
| *B82Y 40/00* | (2011.01) |
| *B82Y 30/00* | (2011.01) |
| *B22F 1/00* | (2006.01) |
| *C22C 5/00* | (2006.01) |
| *C23C 18/14* | (2006.01) |
| *C08K 3/22* | (2006.01) |

(52) U.S. Cl.
CPC ............ *C09D 1/00* (2013.01); *B22F 9/24* (2013.01); *C07F 7/025* (2013.01); *C08G 77/58* (2013.01); *C08K 3/10* (2013.01); *C23C 18/44* (2013.01); *B05D 1/005* (2013.01); *B05D 1/18* (2013.01); *B22F 1/0018* (2013.01); *B22F 1/0062* (2013.01); *B22F 2999/00* (2013.01); *B82Y 30/00* (2013.01); *B82Y 40/00* (2013.01); *C08K 2003/2206* (2013.01); *C22C 5/00* (2013.01); *C23C 18/14* (2013.01); *Y10S 977/773* (2013.01); *Y10S 977/81* (2013.01); *Y10S 977/892* (2013.01); *Y10S 977/896* (2013.01)

(58) Field of Classification Search
None
See application file for complete search history.

(56) References Cited

U.S. PATENT DOCUMENTS

| 7,465,953 B1 | 12/2008 | Koh et al. | |
| 9,257,660 B2 | 2/2016 | Kim et al. | |
| 9,281,484 B2 | 3/2016 | Kim et al. | |
| 2010/0203312 A1* | 8/2010 | Bruckmann | C08G 77/58 |
| | | | 428/221 |
| 2012/0256224 A1* | 10/2012 | Hatanaka | C23C 18/1608 |
| | | | 257/98 |
| 2014/0252307 A1 | 9/2014 | Kim et al. | |
| 2014/0252315 A1 | 9/2014 | Kim et al. | |
| 2015/0179820 A1 | 6/2015 | Kim | |
| 2016/0159988 A1* | 6/2016 | Kim | C08G 77/50 |
| | | | 524/236 |

FOREIGN PATENT DOCUMENTS

CN        104387416        *    3/2015

OTHER PUBLICATIONS

"Formation of Crystalline Nanoclusters of Ag, Cu, Os, Pd, Pt, Re, or Ru in a Silica Xerogel Matrix from Single-Source Molecular Precursors" authored by Carpenter et al. and published in Chem. Mater. 1997, 9, 3164-3170.*
"Size-dependence Enhancement in Electrocatalytic Activity of NiHCF-gold Nanocomposite: Potential Application in Electrochemical Sensing" authored by Pandey et al. and published in Analysy (2012) 137, 3306-3313.*
"Synthesis of Microsized Gold Plates with Nanometer Thickness via a Simple Solution Route using 3-mercaptopropyltrimethoxysilane" authored by Nishi et al., and published in the Journal of the Ceramic Society of Japan (2007) 115 (12), 944-946.*
Kim et al., Facile Preparative Route to Alkanethiolate-Coated Au38 Nanoparticles: Postsynthesis Core Size Evolution, 2007, p. 7853-7858, vol. 25, No. 14, Langmuir.

* cited by examiner

*Primary Examiner* — Marc S Zimmer
(74) *Attorney, Agent, or Firm* — IP & T Group LLP

(57) ABSTRACT

Provided are a compound, including metal atoms for forming metal nano particles through a simple process within a short time at a low production cost for commercial purposes, and a solution including the compound.

13 Claims, 7 Drawing Sheets

SOLUTION FOR FABRICATING NANO PARTICLES

CROSS-REFERENCE TO RELATED APPLICATIONS

This application is a continuation-in-part of U.S. patent application Ser. No. 14/958,366 filed on Dec. 3, 2015, which claims priority to Korean Patent Application No. 10-2014-0172290 and 10-2014-0172291, both filed on Dec. 3, 2014; 10-2014-0187801 and 10-2014-0187804, both filed on Dec. 24, 2014; and 10-2015-0083451 and 10-2015-0083452, both filed on Jun. 12, 2015. The disclosure of each of the foregoing application is incorporated herein by reference in their entirety.

BACKGROUND

1. Field

Various embodiments of the present disclosure relate to a compound for fabricating nano particles, a solution including the compound, and a method for preparing the solution.

2. Description of the Related Art

Nano particles having nano particles exhibit characteristics such as the quantum confinement effect, the Hall-Petch effect, dropping melting point, resonance phenomenon, excellent carrier mobility and so forth as compared to conventional bulk and thin film-type structures. For this reason, nano particles are being applied to chemical batteries, solar cells, semiconductor devices, chemical sensors, photoelectric devices and the like.

Nano particles are fabricated in a top-down method or a bottom-up method. The bottom-up method includes a vapor-liquid-solid (VLS) growth method and liquid growth method. The vapor-liquid-solid growth method is based on a catalytic reaction and includes methods such as the Thermal Chemical Vapor Deposition (thermal-CVD) method, the Metal-Organic Chemical Vapor Deposition (MOCVD) method, the Pulsed Laser Deposition (PLD) method, and the Atomic Layer Deposition (ALD) method. As for the liquid growth method, a self-assembly technology and a hydrothermal method are being suggested.

According to the conventional bottom-up method, nano particles are prepared in advance and then attached to a substrate having a modified surface. However, this method not only has a limitation for decreasing the particle size of nano particles to less than about 5 nm but also deteriorates reproducibility and reliability of a nano semiconductor device using the inherent characteristics of nano particles due to wide distribution of the size of the nano particles. That is, with the method of fabricating nano particles by simply attaching nano particles to a substrate, it is currently impossible to improve the performance of the nano semiconductor device unless nano particles synthesis technology makes remarkable progress.

To overcome this limitation, nano particles may be fabricated in a top-down method such as lithography. However, the use of the top-down method requires a great deal of investment in equipment because a high-end lithography facility is needed. Moreover, since the process is quite complicated, it is not appropriate for mass-production. Also, although an etch process is performed using an electron beam, it is difficult to keep the nano particle size under a predetermined level.

SUMMARY

Various embodiments are directed to a compound containing metal atoms or metal moieties capable of forming nano particles at a low cost using a simple method to attain commercial viability, a solution including the compound, and a method for preparing the solution.

In an embodiment, a compound includes metal atoms for forming metal nano particles, wherein the compound may be represented by the following chemical formula:

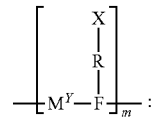

wherein M is a metal atom selected from the group consisting of gold (Au), silver (Ag), ruthenium (Ru), palladium (Pd), platinum (Pt), and copper (Cu), R is ($-CH_2-$)$_n$, F is one selected from the group consisting of sulfur (S), nitrogen (N) and phosphorus (P), X is one selected from the group consisting of a silyl group, a methyl group and a carboxyl group, Y represents an oxidation state of the metal atom in the compound, m is a natural number ranging from 1 to 10, and n is a natural number ranging from 1 to 15.

The M may be gold (Au) and the Y may be +1.
The F may be sulfur (S).
The X may be a silyl group.
The X may be an alkosylsilyl group or an alkylsilyl group.
In another embodiment, a solution for forming metal nano particles may include: the compound in accordance with the embodiment; a solvent; and a stabilizer for preventing metal atoms from being precipitated in the solvent.

The solvent may be selected from the group consisting of methanol, ethanol, 1-propanol, 2-propanol, 1-pentanol, 2-butoxyethanol and ethylene glycol, acetone, 2-butanone and 4-methyl-2-propanone, acetic acid, pentane, hexane, decane, cyclohexane, cyclopentane and 2,2,4-trimethylpentane, 1-butylene, 2-butylene, 1-pentene, 2-pentene, isobutylene, carbon tetrachloride, 1-chlorobutane, 1-chloropentane, 2-chloropropane, 1-chloropropane, bromoethane, chloroform, dichloromethane, 1,2-dichloroethane, 1-nitropropane, nitromethane, and a combination thereof.

The stabilizer may include a basic compound.
The basic compound may be selected from the group consisting of sodium hydroxide, potassium hydroxide, calcium hydroxide, aqueous ammonia, and a combination thereof.

The M may be gold (Au) and the Y is +1.
The F may be sulfur (S).
The X may be a silyl group.
The X may be an alkoxysilyl group or an alkylsilyl group.
In another embodiment, a method for preparing a solution including the compound in accordance with the embodiment may include: reacting a metal precursor with an organic material in the presence of a solvent to form the solution including the compound in accordance with the embodiment; and adding a stabilizer to the solution including the compound in accordance with the embodiment, wherein the metal precursor may be selected from the group consisting of halides, chalcogenides, hydrochlorides, nitrates, sulfates, acetates, or ammonium salts of a metal selected from the group consisting of gold (Au), silver (Ag), ruthenium (Ru), palladium (Pd), platinum (Pt), and copper (Cu), and, wherein the organic material may be a compound including two different functional groups, a first functional group being one or more selected from the group consisting of a thiol group, an amine group, and a phosphine group and a second functional group being one or more selected from the group consisting of a silyl group, a methyl group and a carboxyl group.

The metal precursor may be selected from the group consisting of $HAuCl_4$, $AuCl$, $AuCl_3$, $Au_4Cl_8$, $KAuCl_4$, $NaAuCl_4$, $NaAuBr_4$, $AuBr_3$, $AuBr$, $AuF_3$, $AuF_5$, $AuI$, $AuI_3$, $KAu(CN)_2$, $Au_2O_3$, $Au_2S$, $Au_2S_3$, $AuSe$, $Au_2Se_3$ and a combination thereof.

The organic material may be the organic material may be selected from the group consisting of: 3-mercaptopropyl trimethoxysilane (3-MPTMS), 3-mercaptopropyl triethoxysilane, 11-mercaptoundecyl trimethoxysilane, mercaptomethyl methyl diethoxysilane, (3-aminopropyl)trimethoxysilane (APS), (3-aminopropyl)triethoxysilane, N-(3-aminopropyl)-dimethyl-ethoxysilane (APDMES), mercaptopropyl trimethoxysilane (MPTMS), N-(2-aminoethyl)-3aminopropyltrimethoxysilane, (3-trimethoxysilyl-propyl)diethylenetriamine, and N-(trimethoxysilylpropyl) ethylenediamine triacetic acid.

The solvent may be selected from the group consisting of methanol, ethanol, 1-propanol, 2-propanol, 1-pentanol, 2-butoxyethanol and ethylene glycol, acetone, 2-butanone and 4-methyl-2-propanone, acetic acid, pentane, hexane, decane, cyclohexane, cyclopentane and 2,2,4-trimethylpentane, 1-butylene, 2-butylene, 1-pentene, 2-pentene, isobutylene, carbon tetrachloride, 1-chlorobutane, 1-chloropentane, 2-chloropropane, 1-chloropropane, bromoethane, chloroform, dichloromethane, 1,2-dichloroethane, 1-nitropropane, nitromethane, and a combination thereof.

The stabilizer may include a basic compound.

The basic compound may be selected from the group consisting of sodium hydroxide, potassium hydroxide, calcium hydroxide, aqueous ammonia, and a combination thereof.

The mixing ratio of the metal precursor and the organic material may range from about 1:0.5-15.

DETAILED DESCRIPTION

Figure 1:
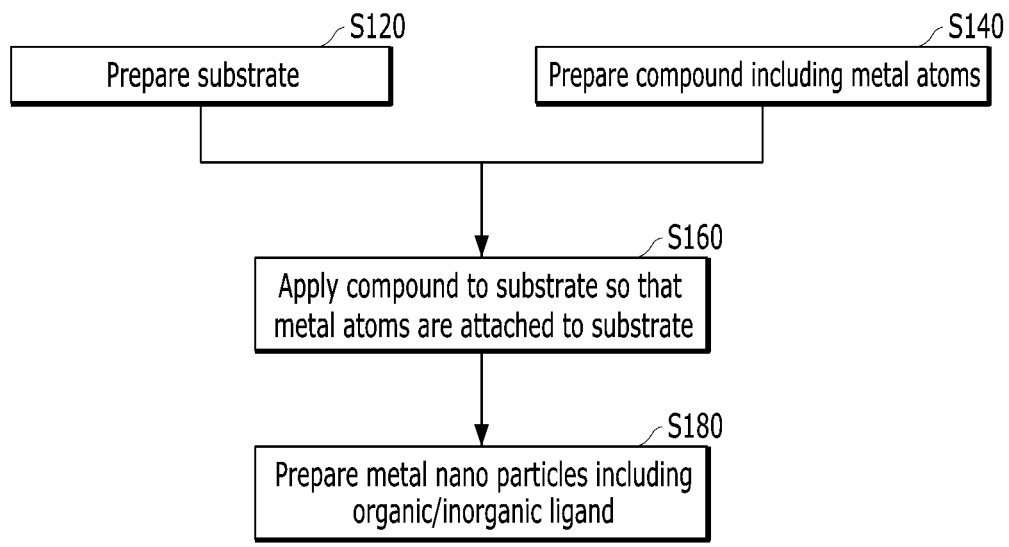
FIG. 1 is a flowchart describing a method for fabricating nano particles in accordance with an embodiment of the present disclosure.

Hereinafter, nano particles and a method for forming the nano particles according to embodiments of the present disclosure will be described in detail with reference to the accompanying drawings. The present disclosure may be embodied in different forms and should not be construed as limited to the embodiments set forth herein. Rather, these embodiments are provided so that this disclosure will be thorough and complete, and will fully convey the scope of the present disclosure to those skilled in the art. In addition, the drawings are not necessarily to scale and, in some instances, proportions may have been exaggerated in order to clearly illustrate features of the embodiments. Throughout the disclosure, reference numerals correspond directly to the like numbered parts in the various figures and embodiments of the present invention.

It should be understood that the meaning of "on" and "over" in the present disclosure should be interpreted in the broadest manner such that "on" means not only "directly on" but also "on" something with an intermediate feature(s) or a layer(s) therebetween, and that "over" means not only directly on top but also on top of something with an intermediate feature(s) or layer(s) therebetween. It is also noted that in this specification, "connected/coupled" refers to one component not only directly coupling another component but also indirectly coupling another component through an intermediate component. In addition, the singular form may include a plural form, and vice versa, as long as it is not specifically mentioned.

Unless otherwise mentioned, all terms used herein, including technical or scientific terms, have the same meaning as understood by those skilled in the technical field to which the present disclosure pertains. In the following description, a detailed description of well-known functions and configurations will be omitted when it may obscure the subject matter of the present disclosure.

FIG. 1 is a flowchart describing a method for fabricating nano particles in accordance with a first embodiment of the present disclosure.

Referring to FIG. 1, the method for fabricating nano particles in accordance with the first embodiment of the present disclosure may include: preparing a substrate in step S120, preparing a solution of a compound including a plurality of metal atoms in step S140, and applying the solution to the substrate so that the metal atoms are attached to the substrate in step S160, and forming at least one metal nano particle by aggregating the metal atoms attached to the substrate in step S180.

Preparation of Substrate (S120)

The preparation of the substrate in the step S120 is described, hereafter, in detail.

The substrate may be a semiconductor substrate, a transparent substrate, or a flexible substrate. The material, structure, and shape of the substrate may differ according to the application device. Also, the substrate may serve as a physical support to the constituent elements of the application device, or the substrate may be a raw material of the constituent elements.

Non-limiting examples of the flexible substrate include a flexible polymer substrate formed of polyethylene terephthalate (PET), polyethylene naphthalate (PEN), polyimide (PI), polycarbonate (PC), polypropylene (PP), triacetyl cellulose (TAC), polyethersulfone (PES), polydimethylsiloxane (PDMS), or a mixture thereof.

When using a semiconductor, the substrate may be an organic semiconductor, an inorganic semiconductor, or a stacked structure thereof.

Non-limiting examples of inorganic semiconductor substrates include a substrate made of a material selected from a group including group 4 semiconductors, which include silicon (Si), germanium (Ge) and silicon germanium (SiGe); group 3-5 semiconductors, which include gallium arsenide (GaAs), indium phosphide (InP) and gallium phosphide (GaP); group 2-6 semiconductors, which include cadmium sulfide (CdS) and zinc telluride (ZnTe); group 4-6 semiconductors, which include lead sulfide (PbS); and a stack of two or more layers made of different materials selected from these materials. From the perspective of crystallography, the inorganic semiconductor substrate may be a monocrystalline material, a polycrystalline material, an amorphous material, or a mixture of a crystalline material and an amorphous material. When an inorganic semiconductor substrate is a stacked structure of two or more layers, each layer may be a monocrystalline material, a polycrystalline material, an amorphous material, or a mixture of a crystalline material and an amorphous material.

Specifically, the inorganic semiconductor substrate may be a semiconductor substrate including a wafer, such as a silicon (Si) substrate, a semiconductor substrate with a surface oxide layer, or a Silicon On Insulator (SOI) substrate including a wafer.

When using an organic semiconductor substrate, the organic semiconductor substrate may be of an n-type organic semiconductor or a p-type organic semiconductor, which are typically used in the fields of organic transistors, organic solar cells, and organic light emitting diodes (OLED). Non-limiting examples of organic semiconductors include fulleren-derivatives, such as copper-phthalocyanine (CuPc), poly(3-hexylthiophene) (P3HT), pentacene, subphthalocyanines (SubPc), fulleren (C60), [6,6]-phenyl-C61-butyric acid methyl ester (PCBM) and [6,6]-phenyl C70-butyric acid methyl ester (PC70BM), and tetra uorotetracyanoquinodimethane (F4-TCNQ). However, these examples of organic semiconductors are not intended to restrict the present disclosure.

The substrate may include a surface layer. For example, the substrate, such as, a silicon substrate, may include a silicon dioxide ($SiO_2$) layer as its surface layer.

Specifically, the surface layer of the substrate may be a single layer of at least one material selected from a group including an oxide, a nitride, an oxynitride, and a silicate, or a stacked layer where two or more of the materials are stacked. Non-limiting examples of the surface layer of the substrate include a single layer of at least one material selected from a group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, a hafnium silicate, a mixture thereof, and a composite thereof, or a stack of two or more layers, each of which is selected from the group.

The surface layer of the substrate may be a metal thin film. The metal thin film may have a thickness of about 100 nm or less. According to an embodiment of the present disclosure, the metal thin film may have a thickness of about 1 nm to 100 nm. When the metal thin film is extremely thin for example, about 1 nm or less, the uniformity of the thin film may deteriorate. Non-limiting examples of the material for the metal thin film, which is used as the surface layer, may include transition metals including noble metals, non-transition metals, or a combination thereof. Herein, examples of the transition metals include Sc, Y, La, Ac, Ti, Zr, Hf, V, Nb, Ta, Cr, Mo, W, Mn, Te, Re, Fe, Ru, Os, Co, Rh, Ir, Ni, Pd, Pt, Cu, Ag, Au, and mixtures thereof, and examples of the non-transition metals include Li, Na, K, Rb, Cs, Fr, Be, Mg, Ca, Sr, Ba, Ra, Zn, Cd, Al, Ga, In, Tl, Ge, Sn, Pb, Sb, Bi, Po, and mixtures thereof.

The surface layer may be formed through a thermal oxidation process, a physical deposition process, or a chemical deposition process. Non-limiting examples of the physical deposition process and the chemical deposition process include sputtering, magnetron-sputtering, e-beam evaporation, thermal evaporation, Laser Molecular Beam Epitaxy (L-MBE), Pulsed Laser Deposition (PLD), vacuum deposition, Atomic Layer Deposition (ALD), and Plasma Enhanced Chemical Vapor Deposition (PECVD).

When a flexible substrate is used, the surface layer of the substrate may be an organic material having a hydroxyl group (—OH).

Moreover, the surface of the substrate may be patterned in diverse forms, which will be described below. According to an embodiment of the present disclosure, a plurality of guide grooves may be patterned. Metal atoms may agglomerate inside the guide grooves to guide where nano particles are situated. The guide grooves on the surface of the substrate may help the arrangement of the nano particles.

Preparation of Compound Including Metal Atoms (S140)

Figure 2:
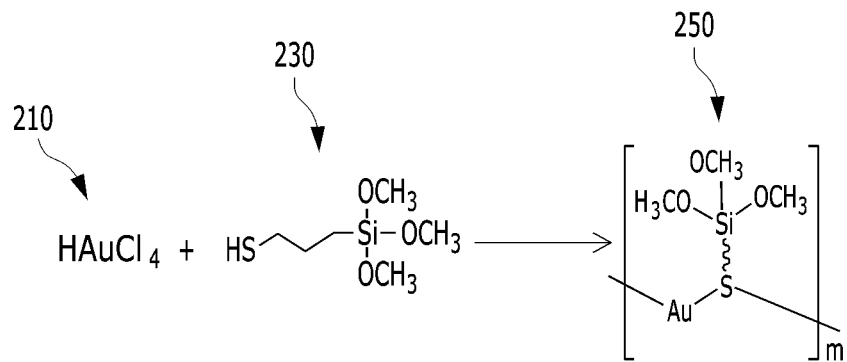
FIG. 2 describes how a compound including metal atoms is prepared.

FIG. 2 describes how a compound 250 including metal atoms or metal moieties, is prepared. Referring to FIG. 2, the compound 250 including metal atoms is prepared by reacting a metal precursor 210 with an organic material 230 in a solvent.

Although the embodiment of FIG. 2 shows an example where $HAuCl_4$ is used as the metal precursor 210, metal precursor 210 may be selected in consideration of the desired nanoparticle material.

For example, the metal precursor may include one or more metal moieties such as transition metals, post-transition metals, and metalloids. In a non-limiting embodiment, the transition metal precursor may be a transition metal salt. Specifically, the transition metal may be one or more selected from a group including gold (Au), silver (Ag), ruthenium (Ru), palladium (Pd), platinum (Pt) and copper (Cu), and the transition metal salt may be selected from a group including halides, chalcogenides, hydrochlorides, nitrates, sulfates, acetates, and ammonium salts of the transition metal. When the transition metal is Au, examples of the transition metal precursor include, but are not limited to, $HAuCl_4$, $AuCl$, $AuCl_3$, $Au_4Cl_8$, $KAuCl_4$, $NaAuCl_4$, $NaAuBr_4$, $AuBr_3$, $AuBr$, $AuF_3$, $AuF_5$, $AuI$, $AuI_3$, $KAu(CN)_2$, $Au_2O_3$, $Au_2S$, $Au_2S_3$, $AuSe$, $Au_2Se_3$, and the like.

The organic material 230 may include two different functional groups, that is, a first functional group and a second functional group. The first functional group may be one or more selected from the group consisting of a thiol group, an amine group, and a phosphine group. The second functional group may be one or more selected from the group consisting of a silyl group, a methyl group and a carboxyl group. The second functional group may be selected in consideration of the uses of the nanoparticles to be prepared in the subsequent process. For example, the second function group can improve affinity for the substrate. In an embodiment, the first functional group may be a thiol group and the second functional group may be a silyl group. The silyl group may include an alkoxysilyl group, an alkylsilyl group or a combination thereof. The embodiment of FIG. 2 shows an example where 3-mercaptopropyltrimethoxysilane (3-MPTMS) including a thiol functional group and a silyl group, is used as the organic material 230. However, other organic materials may be used.

For example, the organic material 230 may be one or more selected from a group including: [3-mercaptopropyl trimethoxysilane (3-MPTMS), 3-mercaptopropyl triethoxysilane, 11-mercaptoundecyl trimethoxysilane, mercaptomethyl methyl diethoxysilane, (3-aminopropyl)trimethoxysilane (APS), (3-aminopropyl)triethoxysilane, N-(3-aminopropyl)-dimethyl-ethoxysilane (APDMES), mercaptopropyltrimethoxysilane (MPTMS), N-(2-aminoethyl)-3aminopropyltrymethoxysilane, (3-trimethoxysilylpropyl)diethylenetriamine, and N-(trimethoxysilylpropyl) ethylenediamine triacetic acid.

The organic material 230 ensures stable isolation between the neighboring nano particles and between the nano particles and the substrate.

The solvent that is used for the reaction of the metal precursor 210 with the organic material 230 may be a hydrophilic solvent or a hydrophobic solvent. When the surface of the substrate is hydrophilic, a hydrophilic solvent may be used. When the surface of the substrate is hydrophobic, a hydrophobic solvent may be used. This enhances the adhesion between the surface of the substrate and the compound in a subsequent process.

Examples of the hydrophilic solvent may include alcohols, such as methanol, ethanol, 1-propanol, 2-propanol, 1-pentanol, 2-butoxyethanol and ethylene glycol, and ketone, such as acetone, 2-butanone and 4-methyl-2-propanone, and acids such as acetic acid.

Examples of the hydrophobic solvent may include cycloalkanes and alkanes, such as pentane, hexane, decane, cyclohexane, cyclopentane and 2,2,4-trimethylpentane, alkenes such as 1-butylene, 2-butylene, 1-pentene, 2-pentene and isobutylene, and substituted alkanes such as carbon tetrachloride, 1-chlorobutane, 1-chloropentane, 2-chloropropane, 1-chloropropane, bromoethane, chloroform, dichloromethane, 1,2-dichloroethane, 1-nitropropane and nitromethane.

As shown in FIG. 2, the compound 250 including metal atoms or metal moieties is prepared by reacting the metal precursor 210 with the organic material 230 in the presence of the solvent.

Although the embodiment of FIG. 2 shows an example where the compound 250 is a polymeric gold-thiol complex, the compound 250 may have the following chemical formula:

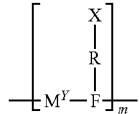

wherein M is a metal atom selected from the group consisting of gold (Au), silver (Ag), ruthenium (Ru), palladium (Pd), platinum (Pt), and copper (Cu), R is ($—CH_2—$)$_n$, F is one selected from the group consisting of sulfur (S), nitrogen (N) and phosphorus (P), X is one selected from the group consisting of a silyl group, a methyl group and a carboxyl group, Y represents an oxidation state of the metal atom in the compound, m is a natural number ranging from 1 to 10, and n is a natural number ranging from 1 to 15. In order to confirm the structure of the compound 250 shown in FIG. 2, an X-ray photoelectron spectroscopy (XPS) analysis and a high performance liquid chromatography (HPLC) mass spectroscopy analysis were performed.

First, samples were prepared as follows. 13.5 mM $HAuCl_4$ and 67.5 mM mercaptopropyltrimethoxysilane (MPTMS) were mixed in the same volume and reacted with each other in the presence of 10 mL of ethanol. As the polymeric chemical bond was formed, the yellowish color of $HAuCl_4$ was changed to transparent colorless. After 1 hour, a solution including the compound 250 was prepared. A total of 10 samples were prepared with the mixing ratio of $HAuCl_4$ to MPTMS from 1:0.5 to 1:15. The mixing ratio is expressed by a mole ratio.

Figure 4:
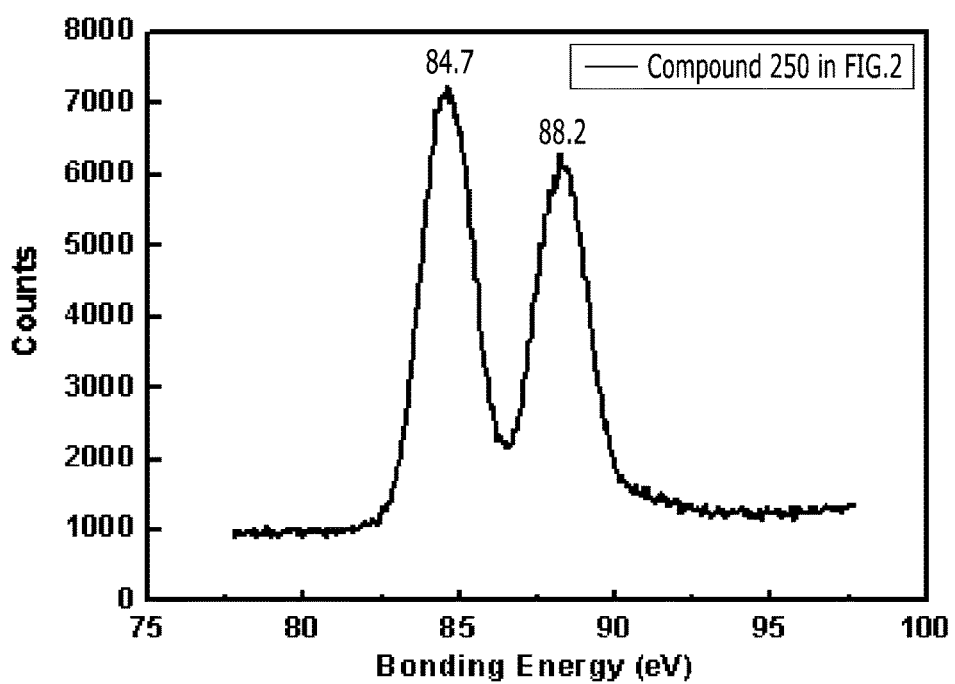
FIG. 4 shows the result of X-ray photoelectron spectroscopy (XPS) analysis to a compound in accordance with an embodiment of the present disclosure.

Then the X-ray photoelectron spectroscopy (XPS) analysis was performed to the samples prepared. FIG. 4 shows the result of X-ray photoelectron spectroscopy (XPS) analysis and Table 1 shows bonding energies of Au depending on the oxidation state of Au.

TABLE 1

| Oxidation state | Bonding energy | |
|---|---|---|
| $Au^0$ | 83.8 eV | 87.5 eV |
| $Au^{+1}$ | 84.6 eV | 88.4 eV |
| $Au^{+3}$ | 86.0 eV | 89.7 eV |

Referring to FIG. 4, doublet peaks of 84.7 eV and 88.2 eV were observed in the samples, which means that the oxidation state of Au in the samples was +1 ($Au^{+1}$) according to Table 1. That is, $Au^{+3}$ in the precursor ($HAuCl_4$) was changed to $Au^{+1}$ in the products (compound 250). Therefore, it can be confirmed that the compound 250 has a structure in which two sulfur (S) groups are bonded to one Au atom as shown in FIG. 2. These results were reproducible in all 10 samples.

Figure 5:
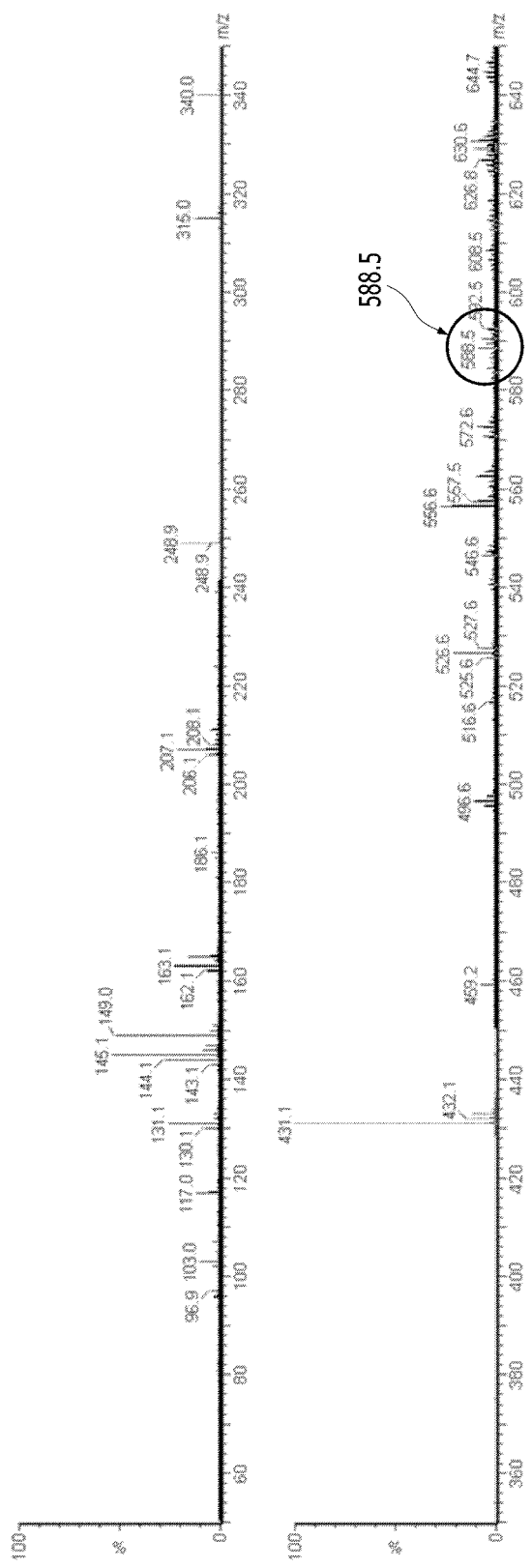
FIG. 5 shows the result of the HPLC mass spectroscopy analysis to a compound in accordance with an embodiment of the present disclosure.

Also, the HPLC mass spectroscopy analysis was performed to the samples prepared. FIG. 5 shows the result of the HPLC mass spectroscopy analysis.

Referring to FIG. 5, the molecular weight of 588.5 (g/mol) was identified, which can correspond to the molecular weight of 587.6 (g/mol) of the structure in which one Au atom is bonded two —S—$(CH_2)_3$—$Si(OCH_3)_3$ groups. Although it is not shown in FIG. 5 due to the detection limit of the equipment, those skilled in the art can obviously expect that the compounds 250 having the various repeating unit m can exist. Further, the repeating unit m may be controlled by adjusting the mixing ratio of the metal precursor 210 and the organic material 230.

In view of the results shown in FIGS. 4 and 5, it can be clearly recognized by those skilled in the art that the compound 250 has a polymeric structure in which each Au atom is bonded two —S—$(CH_2)_3$—$Si(OCH_3)_3$ groups.

The content of the metal atoms in the compound 250 may be controlled by adjusting the mixing ratio of the metal precursor 210 and the organic material 230. This may be one of the significant factors for controlling the diameter of the nano particles prepared in the subsequent process. Additionally, the concentration of the compound 250 in a solution may be one of the significant factors for controlling the density of the nano particles formed over the substrate and the number of the nano particle layers. For example, when the ratio of the metal precursor 210 and the organic material 230 is controlled to be between about 1:3 to 1:10, nano particles having a diameter of about 1.6±0.2 nm to 1.1±0.2 nm may be prepared, respectively.

Meanwhile, after a predetermined time passes, aggregation may occur among the metal atoms and among ligands so that a solution of the compound including metal atoms may become unstable. Thus, the transparent solution may be changed to hazy and precipitation may occur. To prevent the precipitation, a stabilizer may be added to the solution of the compound 250 after performing the reaction of the metal precursor 210 with the organic material 230. According to an embodiment of the present disclosure, the stabilizer may include a basic compound, which may be one selected from a group including sodium hydroxide, potassium hydroxide, calcium hydroxide, and aqueous ammonia. The stabilizer may be added in a mole ratio ranging from 0.01 to 0.5 based on the metal precursor 210.

The advantageous effects obtained by using the stabilizer according to the embodiment of the present disclosure will be explained in detail with reference to FIGS. 6A, 6B and 7.

Figure 6A:
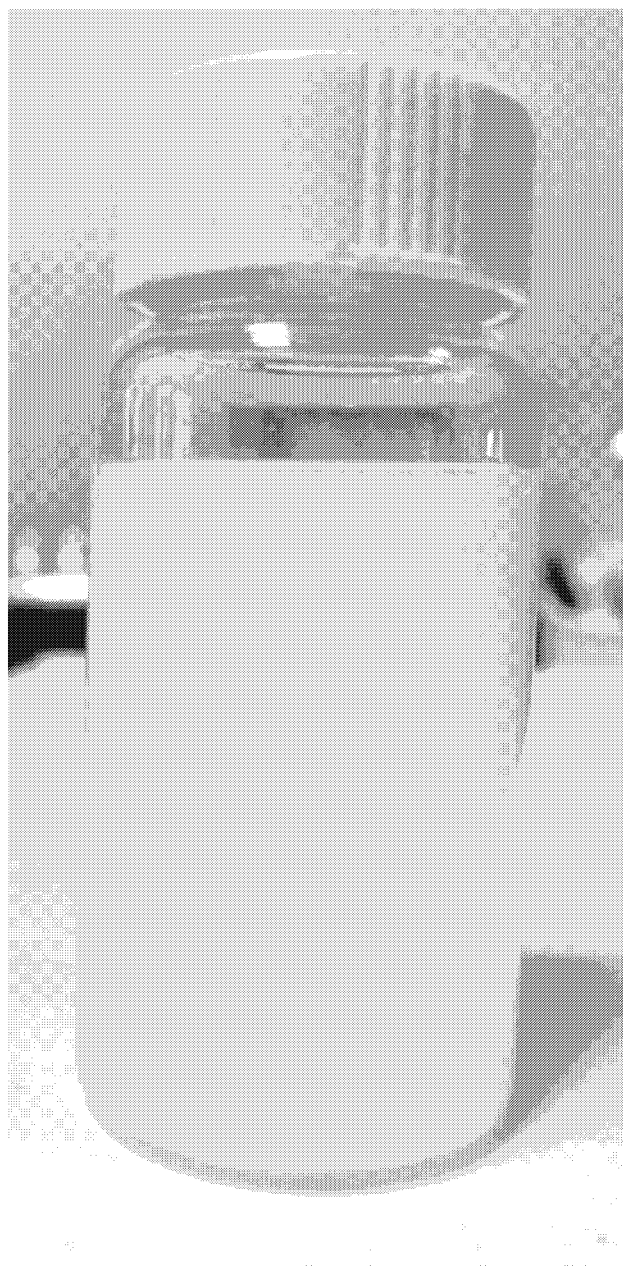
FIGS. 6A and 6B shows the result of a stability test of a solution in accordance with a comparative example.
Figure 6B:
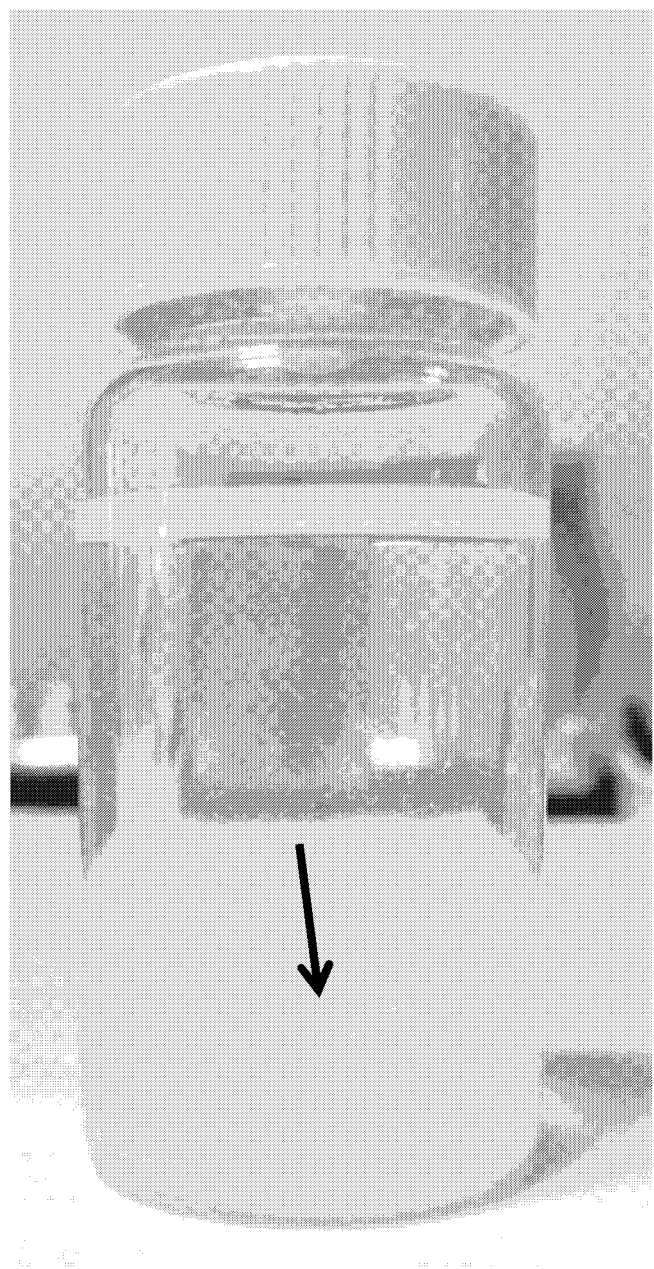
Figure 7:
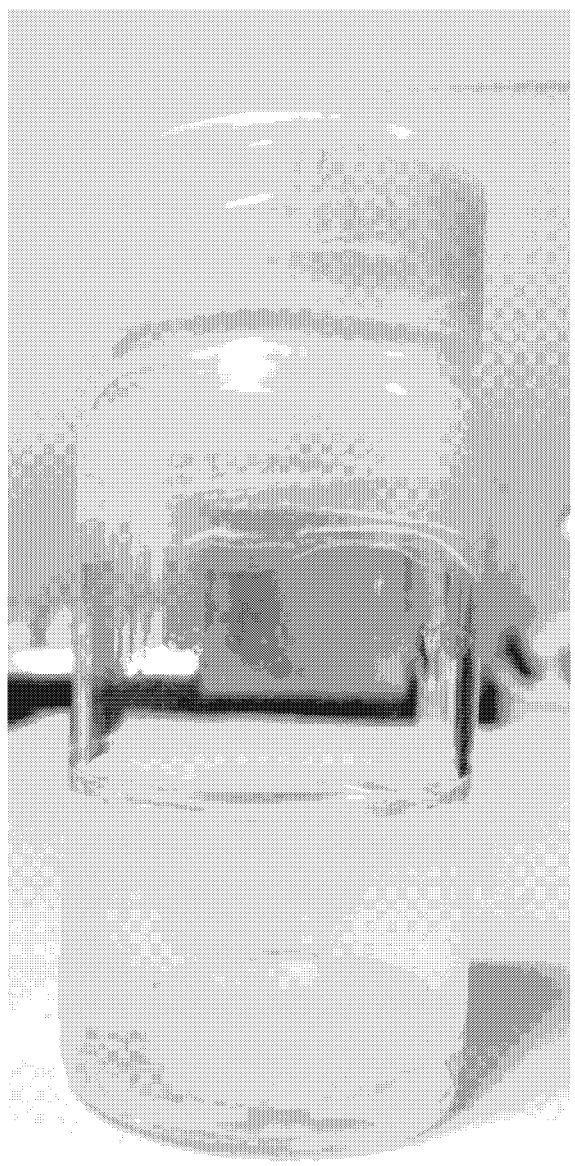
FIG. 7 shows the result of a stability test of a solution in accordance with an embodiment of the present disclosure.

FIGS. 6A and 6B show the result of a stability test of a solution in accordance with the comparative example, and FIG. 7 show the result of a stability test of a solution in accordance with the embodiment of the present disclosure. The solution shown in FIGS. 6A and 6B was prepared as follows. 13.5 mM HAuCl4 and 67.5 mM MPTMS were mixed in the same volume and reacted with each other in the presence of 10 mL of ethanol. As the polymeric chemical bond was formed, the yellowish color of $HAuCl_4$ was changed to transparent colorless. After 1 hour, a solution containing the compound 250 was obtained. The solution shown in FIG. 7 was prepared similarly to the solution shown in FIGS. 6A and 6B except that, after 1 hour of the reaction, 2 mL of 10% $NH_4OH$ as a stabilizer was added to the solution containing the compound 250.

Referring to FIG. 6A, it was observed that the transparent solution was changed to hazy and the solution became unstable after 2 hours due to aggregation. Further, referring to FIG. 6B, it was also observed that precipitation indicated by the arrow occurred after 3 days.

Referring to FIG. 7, unlike the solution shown in FIGS. 6A and 6B, it was observed that the transparent solution containing the compound was stably maintained and no precipitation occurred.

As such, in accordance with the embodiment of the present disclosure, the stabilizer is added to the solution of the compound 250 so that aggregation and precipitation can be prevented to maintain the stability of the solution.

Application of Compound to Substrate (S160)

When the substrate and the compound are prepared, the compounds are applied to the substrate to attach the metal atoms included in the compound onto the substrate.

The application of the compound to the substrate may be performed diversely. According to an embodiment, the substrate may be coated with the compound through a spin-coating process or a dipping process. As the compound is applied to the substrate, the metal atoms included in the compound are attached onto the substrate.

The number of the metal atoms which is attached to the substrate may be adjusted by controlling the speed and time of the spin-coating process, which will be described below. This may be one of the significant methods for controlling the diameter of the nano particles.

Metal Atoms being Formed into Metal Nano Particles (S180)

The metal atoms attached to the substrate become metal nano particles through reduction and growth. The growth, herein, includes nucleation and agglomeration.

When energy is applied to the metal atoms, the metal atoms are reduced and grown into particles. The energy that is applied to form the nano particles may be one or more selected from a group including heat energy, chemical energy, light energy, vibration energy, atomic beam energy, electron beam energy, and radiation energy.

Thermal energy may include Joule heat and may be applied directly or indirectly. Direct application of thermal energy may be performed in a state in which a heat source and the substrate having metal atoms fixed thereto come into physical contact with each other. Indirect application of thermal energy may be performed in a state in which a heat source and the substrate having metal atoms fixed thereto do not come into physical contact with each other. Non-limiting examples of direct application include a method of placing a heating element, which generates Joule heat by the flow of electric current, beneath the substrate and transferring thermal energy to the metal atoms through the substrate. Non-limiting examples of indirect application include using a conventional heat-treatment furnace including a space in which an object such as a tube to be heat-treated is placed, a heat insulation material that surrounds the space to prevent heat loss, and a heating element placed inside the heat insulation material. A non-limiting example of indirect heat application is seen in the method of placing a heating element at a predetermined distance above the substrate where the metal atoms are fixed, and transferring thermal energy to the metal atoms through a fluid, including air, present between the substrate and the heating element.

Light energy may include light having a wavelength ranging from extreme ultraviolet to near-infrared, and application of light energy may include irradiation with light. According to a non-limiting embodiment, a light source may be placed above the substrate having the metal atoms fixed thereto, at a predetermined distance from the metal atoms, and light from the light source may be irradiated onto the metal atoms.

Vibration energy may include microwaves and/or ultrasonic waves. Application of vibration energy may include irradiation with microwaves and/or ultrasonic waves. According to a non-limiting embodiment, a microwave and/or ultrasonic wave source may be placed above the substrate having the metal atoms fixed thereto, at a predetermined distance from the metal atoms, and microwaves and/or ultrasonic waves from the source may be irradiated onto the metal atoms.

Radiation energy may include one or more selected from a group including α rays, β rays and γ rays, and may be β rays and/or γ rays for reduction of the metal atoms. According to a non-limiting embodiment, a radiation source may be placed above the substrate, having the metal atoms fixed thereto, at a predetermined distance from the metal atoms and radiation from the source may be irradiated onto the metal atoms.

Energy may be kinetic energy of a particle beam, and the particle beam may include an atomic beam and/or an electron beam. In terms of the reduction of the metal atoms, the atoms of the beam may be negatively charged. According to a non-limiting embodiment, an atom or electron source may be placed above the substrate, having the metal atoms fixed thereto, at a predetermined distance from the metal atoms, and an atomic beam and/or electron beam may be applied to the metal atoms using an accelerating element that provides an electric field or magnetic field that accelerates atoms or electrons in the direction of the metal atoms.

Chemical energy is the Gibbs free energy difference between before and after a chemical reaction, and the chemical energy may include reduction energy. Chemical energy may include the energy of a reduction reaction with a reducing agent and may mean the energy of a reduction reaction in which the metal atoms in the precursor are reduced by the reducing agent. According to a non-limiting embodiment, application of chemical energy may be a reduction reaction in which the reducing agent is brought to the substrate having the metal atoms fixed thereto. The reducing agent may be supplied in the liquid or gaseous state.

In a preparation method according to an embodiment of present disclosure, application of energy may include simultaneously or sequentially applying two or more selected from a group including heat energy, chemical energy, light energy, vibration energy, atomic beam energy, electron beam energy, and radiation energy.

In a specific embodiment of simultaneous application, application of heat may be performed simultaneously with application of a particle beam. The particles of the particle beam may be heated by heat energy. In another specific embodiment of simultaneous application, application of heat may be performed simultaneously with application of a reducing agent. In still another embodiment of simultaneous application, application of a particle beam may be performed simultaneously with application of infrared rays or with application of microwaves.

Sequential application may mean that one kind of energy is applied and then followed by application of another kind of energy. It may also mean that different kinds of energy are continuously or discontinuously applied to the metal atoms. It is preferable that reduction of the metal atoms fixed to the substrate in mediation of an organic material be performed before formation of nano particles, and thus in a specific embodiment of sequential application, heat may be applied after addition of a reducing agent or after application of a negatively charged particle beam.

In a non-limiting practical embodiment, application of energy may be performed using a rapid thermal processing (RTP) system, including a tungsten-halogen lamp, and the rapid thermal processing may be performed at a heating rate of about 50 to 150° C./sec. Also, rapid thermal processing may be performed in a reducing atmosphere or an inert gas atmosphere.

In another non-limiting practical embodiment, application of energy may be performed by bringing a solution of a reducing agent into contact with the metal atoms followed by thermal processing using the rapid thermal processing system in a reducing atmosphere or an inert gas atmosphere.

In a non-limiting practical embodiment, application of energy may be performed by generating an electron beam from an electron beam generator in a vacuum chamber and accelerating the generated electron beam to the metal atoms. The electron beam generator may be of a square type or a linear gun type. The electron beam may be produced by generating plasma from the electron beam generator and extracting electrons from the plasma using a shielding membrane. In addition, a heating element may be provided on a holder for supporting the substrate in the vacuum chamber, and heat energy may be applied to the substrate by this heating element before, during and/or after application of the electron beam.

When the desired nano particles are metal nano particles, the metal nano particles may be prepared upon the application of energy as described above. The nano particles to be prepared are metal nano particles or metal compound nano particles. The metal compound nano particles may be prepared by supplying an element different from the metal atoms during or after the application of the above-described energy. Specifically, the metal compound nano particles may include metal oxide nano particles, metal nitride nano particles, metal carbide nano particles or intermetallic compound nano particles. More specifically, the metal compound nano particles may be prepared by supplying a different element in the gaseous or liquid state during or after the application of the above-described energy. In a specific embodiment, metal oxide nano particles in place of metal nano particles may be prepared by supplying an oxygen source including oxygen gas during the application of energy. In addition, metal nitride nano particles in place of metal nano particles may be prepared by supplying a nitrogen source including nitrogen gas during the application of energy. Metal carbide nano particles may be prepared by supplying a carbon source, including $C_1$-$C_{10}$ hydrocarbon gas during the application of energy, and intermetallic compound nano particles may be prepared by supplying a precursor gas containing a different element, which provides an intermetallic compound, during the application of energy. Specifically, the intermetallic compound nano particles may be prepared by carbonizing, oxidizing, nitrifying or alloying the metal nano particles prepared by the application of the above-described energy.

The density of nano particles that is, the number of nano particles per unit surface area of the channel region, the particle size, and particle size distribution may be controlled by adjusting one or more factors selected from the energy application conditions, including the type, magnitude, temperature, and duration of energy application.

Moreover, it is possible to prepare not only metal nano particles but also metal oxide nano particles, metal nitride nano particles, metal carbide nano particles, or intermetallic compound nano particles by supplying a heterogeneous atom source while energy is applied or after energy is applied to change metal nano particles into metal compound nano particles.

In a preparation method according to an embodiment of the present disclosure, i) the size of nano particles may be controlled by supplying an organic surfactant that is bonded to or adsorbed on the metal atoms, followed by the application of energy. Otherwise, ii) the size of nano particles may be controlled during the growth of the metal atoms by supplying an organic surfactant that is to be bonded to or adsorbed on the metal atoms during the application of energy. This supply of the organic surfactant may be optionally performed during the preparation process. One or a plurality of organic surfactants may be used as the organic surfactant that is applied before or during the application of energy.

To more effectively inhibit the mass transfer of the metal atoms, a first organic material and a second organic material that are different from each other may be used as the organic surfactant.

The first organic material may be a nitrogen- or sulfur-containing organic material. For example, the sulfur-containing organic material may include a linear or branched hydrocarbon compound having a thiol group as an end functional group. In a specific example, the sulfur-containing organic material may be one or more selected from a group including HS—$C_n$—$CH_3$ (n is an integer ranging from 2 to 20), n-dodecyl mercaptan, methyl mercaptan, ethyl mercaptan, butyl mercaptan, ethylhexyl mercaptan, isooctyl mercaptan, tert-dodecyl mercaptan, thioglycolacetic acid, mercaptopropionic acid, mercaptoethanol, mercaptopropanol, mercaptobutanol, mercaptohexanol and octyl thioglycolate.

The second organic material may be a phase-transfer catalyst-based organic material, for example, quaternary ammonium or a phosphonium salt. More specifically, the second organic material may be one or more selected from a group including tetraocylyammonium bromide, tetraethylammonium, tetra-n-butylammonium bromide, tetramethylammonium chloride, and tetrabutylammonium fluoride.

This organic surfactant makes it possible to inhibit the transfer of the metal atoms during the application of energy to thereby form more uniform and finer nano particles. Since the metal atoms bond with the organic surfactant, these metal atoms require higher activation energy compared to when they diffuse without the organic surfactant in order to participate in nucleation or growth. Thus, the diffusion of the metal atoms may become slower and the number of the metal atoms that participate in the growth of nuclei may be decreased.

In a preparation method according to an embodiment of the present disclosure, energy may be applied to the entire area simultaneously or applied to a portion of the region having the metal atoms. When energy is applied to a portion of the metal atom region, energy may be irradiated in a spot, line or predetermined plane shape. In a non-limiting embodiment, energy may be applied that is, irradiated in spots while the entire metal atom region may be scanned. The application of energy to a portion of the metal atom region may include not only irradiating energy in a spot, line or plane shape while the entire metal atom region is scanned, but also where energy is applied that is irradiated only on a portion of the metal atom region. As described above, a pattern of nano particles may be formed by applying energy to a portion. Therefore, application that is, irradiation of energy to a portion of a region makes it possible to form a pattern of nano particles.

Figure 3A:
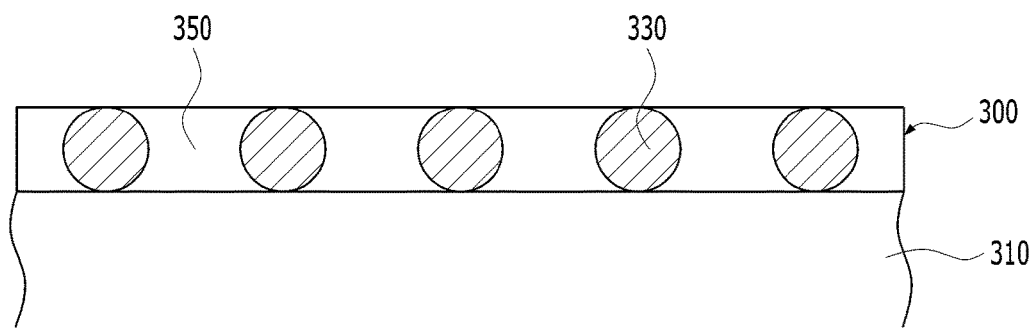
FIG. 3A is a cross-sectional view illustrating a nano particle layer formed over a substrate.

FIG. 3A is a cross-sectional view illustrating a nano particle layer formed over a substrate.

Referring to FIG. 3A, a plurality of metal nano particles 330 form a nano particle layer 300 over a substrate 310 by being spaced apart from each other. The nano particle layer 300 may be one-nanoparticle-thick layer. That is the nano particle layer 300 may be formed as thick as a diameter of a single nanoparticle. In another embodiment, it may be a multi-layer of two nanoparticle layers or three nanoparticle layers.

Figure 3B:
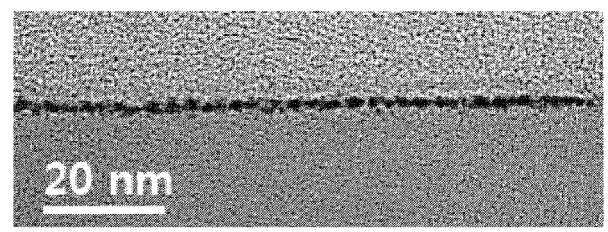
FIGS. 3B and 3C show transmission electron microscopy (TEM) images of a nano particle layer formed over a substrate.
Figure 3C:
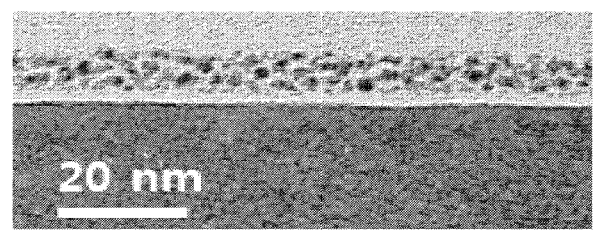

FIGS. 3B and 3C show transmission electron microscopy (TEM) images of a nano particle layer formed over a substrate. FIG. 3B shows a TEM image of a single layer and FIG. 3C shows a multi-layer.

Each of the nano particles may have a particle diameter of about 0.5 nm to 5 nm with narrow size distribution.

The diameter of the metal nano particles 330 may be determined based on the concentration of the metal atoms included in a polymer used for the preparation process. That is, the diameter of the nano particles may be controlled by adjusting the mixing ratio of a metal precursor and an organic material when the polymer is prepared. For example, when the mixing ratio of the metal precursor and the organic material falls in the range of about 1:3 to 1:10, nano particles having a diameter of about 1.6±0.2 nm to 1.1±0.2 nm may be prepared, respectively.

It is also possible to control the diameter and density of the nano particles by controlling a spin coating rate and time when the substrate is spin-coated with the compound. Additionally, the diameter of the nano particles may be controlled by controlling the conditions of energy application that is performed to reduce and grow the metal atoms.

As described earlier, the nano particle layer 300 may be formed in a mono-layer or a multi-layer, and the nano particle layer 300 may be formed in a mono-layer or multi-layer structure by controlling the concentration of the metal atoms such as, ions in the inside of the compound or by controlling the conditions of the spin-coating process.

Referring back to FIG. 3, the nano particle layer 300 may include an insulation material 350 covering the metal nano particles 330.

After the formation of the metal nano particles 330, a moiety derived from the organic material in the polymer or an organic surfactant may remain around the metal nano particles 330 or may be removed. While the moiety derived from the organic material remains or while the moiety derived from the organic material is removed, a protective layer may be formed to fix and protect the metal nano particles 330, and the protective layer may be an inorganic material.

Therefore, the insulation material 350 may be the moiety derived from the organic material in the polymer, the organic surfactant, or an inorganic material such as an oxide or a nitride.

Since a solution according to an embodiment of the present invention includes metal atoms, nano particles may be formed over a substrate after a substrate is coated with the solution containing the compound.

Even though nano particle synthesis technology has made great progress, in terms of thermodynamics, nano particles that are synthesized in the exterior inevitably have a variation in particle size. The size difference or variation between the nano particles becomes greater as the reaction during the synthesis grows bigger. Therefore, in order to produce mono dispersed (i.e., narrow core size distribution) nanoparticles in poly dispersed (i.e., different core size distribution) nano particles, it is required additional complicated process such as separation via solvent fractionation methodology. Furthermore, the existing known technology of attaching externally pre-formed nano particles, which are not formed over a substrate but in the outside of the substrate, onto a substrate has limitations in the preparation of uniform nano particles. Also, a method of preparing nano particles in a top-down method through an etch process has limitations in mass-production for commercial purposes even though lithography technology is highly advanced and it becomes possible to prepare particles of about 5 nm or smaller. This is due to the method being high-cost, complicated and requiring precise control.

When nano particles are prepared using a polymer solution in accordance with an embodiment of the present invention, the nano particles are directly prepared in a small reaction field that corresponds to a surface area of the substrate. Therefore, the nano particles may be formed with a size that is extremely uniform and delicately controlled in a high density. Furthermore, since the nano particles are formed by applying energy to metal atoms after the metal atoms are fixed onto the substrate through a process of coating the substrate with the compound including the metal atoms, it is simple, easy and capable of mass-producing the nano particles at a low cost within a short production time. Also, since the nucleation and growth are carried out by applying energy while the metal atoms are fixed onto the substrate, the migration of the metal atoms are uniformly suppressed in overall, which leads to formation of uniform and fine nano particles. Specifically, only metal atoms bonded to an organic material may be supplied as a metal source that is required for nucleation and growth of a material for forming nano particles. That is, the material for forming nano particles may be supplied only by the migration of the metal atoms bonded to the organic material. In addition, since the metal atoms bonded to the organic material hardly migrate beyond a predetermined distance and participate in the nucleation and growth, the reaction field of each nano particle is limited to the surroundings of each nucleus. Therefore, nano particles having uniform and fine particle size may be formed over the substrate in a high density and uniformly spaced apart from each other. The space between the metal nano particles may correspond to the diffusion distance of the metal atoms that contribute to the nucleation and growth of the nano particles.

According to the embodiments of the present disclosure, nano particles may be prepared by using a polymeric metal-thiol complex. Also, patterned nano particles may be prepared by attaching metal atoms through a direct coating process for coating a substrate, such as a patterned silicon substrate, a flexible polymer film, a transparent glass and the like, with a polymer including metal atoms that reduces and grows the metal atoms. As a result, it is possible to reduce production cost and achieve mass-production with a short production time.

Although various embodiments have been described for illustrative purposes, it will be apparent to those skilled in the art that various changes and modifications may be made without departing from the spirit and scope of the disclosure as defined in the following claims.

What is claimed is:

1. A solution for forming metal nano particles, comprising:
a compound having the following chemical formula:

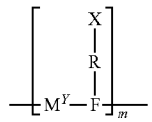

wherein M is a metal atom of gold (Au), R is (—$CH_2$—)$_n$, F is selected from the group consisting of sulfur (S), nitrogen (N) and phosphorus (P), X is a silyl group, Y represents an oxidation state of the metal atom in the compound of +1, m is a natural number ranging from 1 to 10, and n is a natural number ranging from 1 to 15;
a solvent; and
a stabilizer for preventing metal atoms from being precipitated in the solvent.

2. The solution of claim 1, wherein the solvent is selected from the group consisting of methanol, ethanol, 1-propanol, 2-propanol, 1-pentanol, 2-butoxyethanol and ethylene glycol, acetone, 2-butanone and 4-methyl-2-propanone, acetic acid, pentane, hexane, decane, cyclohexane, cyclopentane and 2,2,4-trimethylpentane, 1-butylene, 2-butylene, 1-pentene, 2-pentene, isobutylene, carbon tetrachloride, 1-chlorobutane, 1-chloropentane, 2-chloropropane, 1-chloropropane, bromoethane, chloroform, dichloromethane, 1,2-dichloroethane, 1-nitropropane, nitromethane, and a combination thereof.

3. The solution of claim 1, wherein the stabilizer includes a basic compound.

4. The solution of claim 3, wherein the basic compound is selected from the group consisting of sodium hydroxide, potassium hydroxide, calcium hydroxide, aqueous ammonia, and a combination thereof.

5. The solution of claim 1, wherein the F is sulfur (S).

6. The solution of claim 1, wherein the X is an alkoxysilyl group or an alkylsilyl group.

7. A method for preparing a solution including a compound having the following chemical formula:

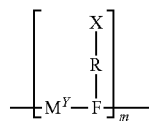

wherein M is a metal atom of gold (Au), R is (—$CH_2$—)$_n$, F is selected from the group consisting of sulfur (S), nitrogen (N) and phosphorus (P), X is a silyl group, Y represents an oxidation state of the metal atom in the compound of +1, m is a natural number ranging from 1 to 10, and n is a natural number ranging from 1 to 15, the method comprising:
reacting a metal precursor with an organic material in the presence of a solvent to form the solution including the compound; and
adding a stabilizer to the solution including the compound,
wherein the metal precursor is selected from the group consisting of halides, chalcogenides, hydrochlorides, nitrates, sulfates, acetates, or ammonium salts of gold (Au), and,
wherein the organic material is a compound including two different functional groups, a first functional group being one or more selected from the group consisting of a thiol group, an amine group, and a phosphine group and a second functional group being a silyl group.

8. The method of claim 7, wherein the metal precursor is selected from the group consisting of $HAuCl_4$, $AuCl$, $AuCl_3$, $Au_4Cl_8$, $KAuCl_4$, $NaAuCl_4$, $NaAuBr_4$, $AuBr_3$, $AuBr$, $AuF_3$, $AuF_5$, $AuI$, $AuI_3$, $KAu(CN)_2$, $Au_2O_3$, $Au_2S$, $Au_2S_3$, $AuSe$, $Au_2Se_3$ and a combination thereof.

9. The method of claim 7, wherein the organic material is selected from the group consisting of: 3-mercaptopropyl trimethoxysilane (3-MPTMS), 3-mercaptopropyl triethoxysilane, 11-mercaptoundecyl trimethoxysilane, mercaptomethyl methyl diethoxysilane, (3-aminopropyl)trimethoxysilane (APS), (3-aminopropyl)triethoxysilane, N-(3-aminopropyl)-dimethyl-ethoxysilane (APDMES), mercaptopropyl trimethoxysilane (MPTMS), N-(2-aminoethyl)-3aminopropyltrimethoxysilane, (3-trimethoxysilylpropyl)diethylenetriamine, and N-(trimethoxysilylpropyl) ethylenediamine triacetic acid.

10. The method of claim 7, wherein the solvent is selected from the group consisting of methanol, ethanol, 1-propanol, 2-propanol, 1-pentanol, 2-butoxyethanol and ethylene glycol, acetone, 2-butanone and 4-methyl-2-propanone, acetic acid, pentane, hexane, decane, cyclohexane, cyclopentane and 2,2,4-trimethylpentane, 1-butylene, 2-butylene, 1-pentene, 2-pentene, isobutylene, carbon tetrachloride, 1-chlorobutane, 1-chloropentane, 2-chloropropane, 1-chloropropane, bromoethane, chloroform, dichloromethane, 1,2-dichloroethane, 1-nitropropane, nitromethane, and a combination thereof.

11. The method of claim 7, wherein the stabilizer includes a basic compound.

12. The method of claim 11, wherein the basic compound is selected from the group consisting of sodium hydroxide, potassium hydroxide, calcium hydroxide, aqueous ammonia, and a combination thereof.

13. The method of claim 7, wherein a mixing ratio of the metal precursor to the organic material ranges from about 1:3-12.

* * * * *